(12) United States Patent
Buesseler et al.

(10) Patent No.: US 8,636,188 B2
(45) Date of Patent: Jan. 28, 2014

(54) FASTENER DEPLOYMENT SYSTEM

(71) Applicants: Ryan K. Buesseler, Bemidji, MN (US);
David B. Hom, Cincinnati, OH (US);
Arthur G. Erdman, New Brighton, MN (US)

(72) Inventors: Ryan K. Buesseler, Bemidji, MN (US);
David B. Hom, Cincinnati, OH (US);
Arthur G. Erdman, New Brighton, MN (US)

( * ) Notice: Subject to any disclaimer, the term of this patent is extended or adjusted under 35 U.S.C. 154(b) by 0 days.

(21) Appl. No.: 13/780,484

(22) Filed: Feb. 28, 2013

(65) Prior Publication Data

US 2013/0168434 A1 Jul. 4, 2013

Related U.S. Application Data

(62) Division of application No. 12/937,361, filed as application No. PCT/US2009/002235 on Apr. 9, 2009, now Pat. No. 8,387,849.

(60) Provisional application No. 61/123,807, filed on Apr. 11, 2008.

(51) Int. Cl.
*A61B 17/068* (2006.01)

(52) U.S. Cl.
USPC ......... 227/175.1; 227/19; 227/67; 227/176.1; 606/90; 606/143; 606/219

(58) Field of Classification Search
USPC .................... 227/19, 175.1, 176.1, 180.1, 67; 606/90, 139, 143, 151, 153, 219
See application file for complete search history.

(56) References Cited

U.S. PATENT DOCUMENTS

| | | | |
|---|---|---|---|
| 3,650,452 A | 3/1972 | Finke | |
| 4,241,861 A | 12/1980 | Fleischer | |
| 4,425,915 A | 1/1984 | Ivanov | |
| 4,522,207 A | 6/1985 | Klieman et al. | |
| 4,562,839 A | 1/1986 | Blake, III et al. | |
| 4,784,137 A | 11/1988 | Kulik et al. | |
| 5,040,715 A | 8/1991 | Green et al. | |
| 5,067,958 A | 11/1991 | Sandhaus | |
| 5,366,134 A | 11/1994 | Green et al. | |
| 5,423,858 A | 6/1995 | Bolanos et al. | |
| 5,573,169 A | 11/1996 | Green et al. | |
| 5,833,700 A | 11/1998 | Fogelberg et al. | |
| 5,915,615 A | 6/1999 | Bauer | |
| 6,446,854 B1 | 9/2002 | Remiszewski et al. | |
| 7,028,878 B2 | 4/2006 | Bauer | |
| 7,572,266 B2 | 8/2009 | Young et al. | |
| 7,621,926 B2 | 11/2009 | Wixey et al. | |
| 7,721,933 B2 | 5/2010 | Ehrenfels et al. | |
| 8,074,857 B2 | 12/2011 | Peterson et al. | |
| 8,387,849 B2 * | 3/2013 | Buesseler et al. | 227/175.1 |
| 2004/0230198 A1 | 11/2004 | Manzi et al. | |
| 2006/0163313 A1 | 7/2006 | Larson | |

OTHER PUBLICATIONS

Search Report and Written Opinion for PCT/US2009/002235, mailed on Sep. 25, 2009.

* cited by examiner

*Primary Examiner* — Scott A. Smith
(74) *Attorney, Agent, or Firm* — Vidas, Arrett & Steinkraus, P.A.

(57) ABSTRACT

This document discloses, among other things, a long reach, side ejecting fastener placement apparatus suitable for use in nasal septal surgery. A first linear member carries a fastener body and a second linear member delivers a fastener retainer or provides support for placement of the fastener body. In various examples, the fastener includes a single stud rivet or includes a two legged staple. A mechanical linkage coupled to the handle provides a linear force for placement and deployment of a fastener.

15 Claims, 17 Drawing Sheets

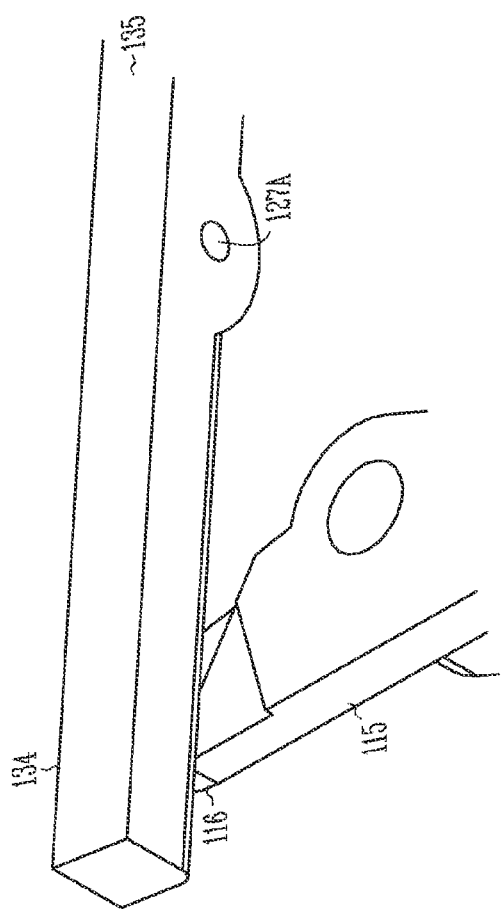
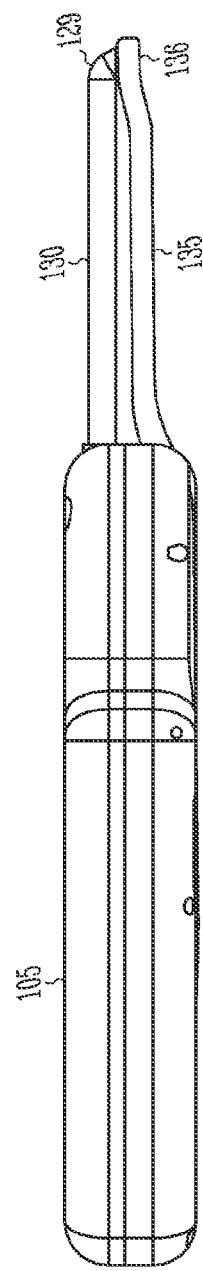

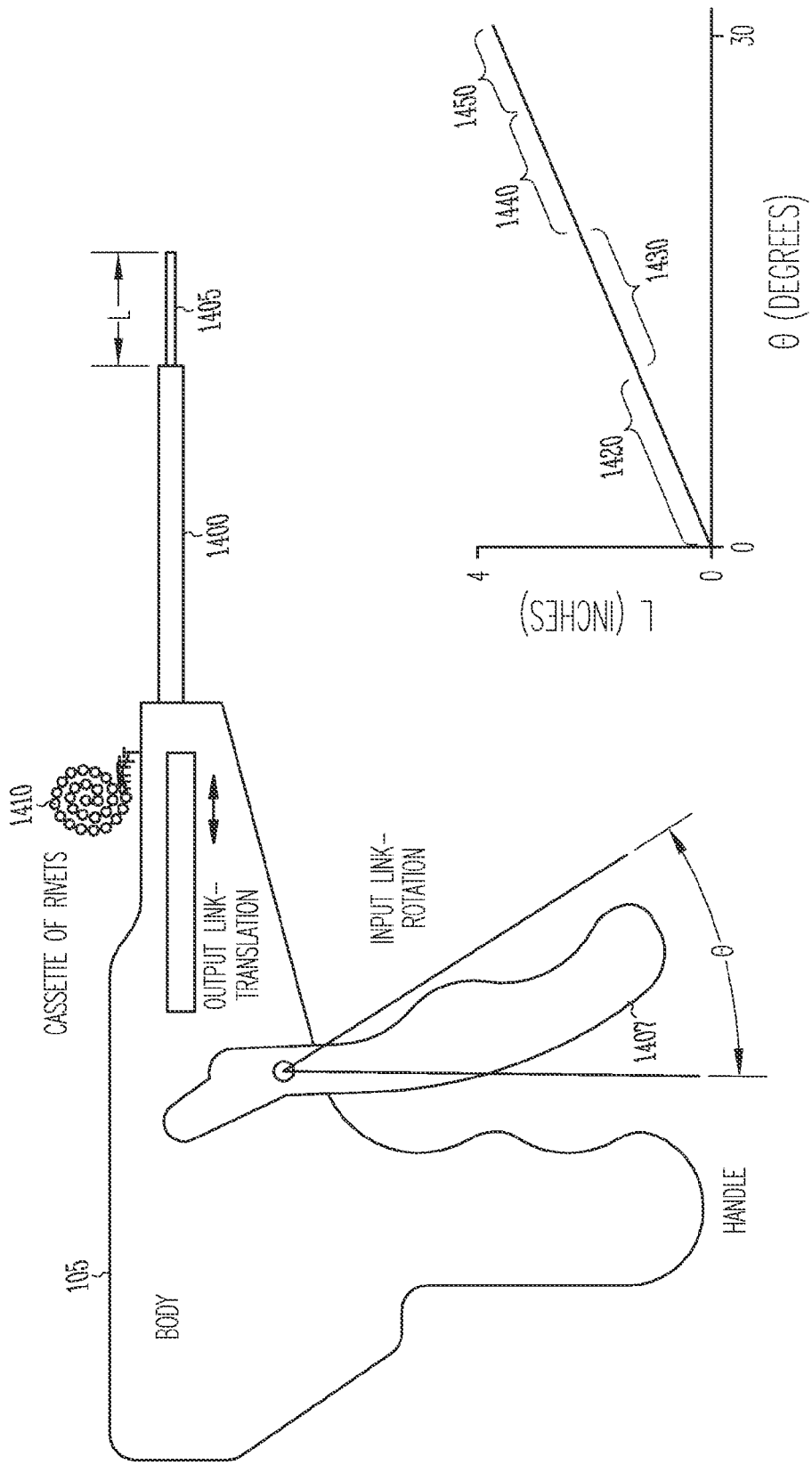

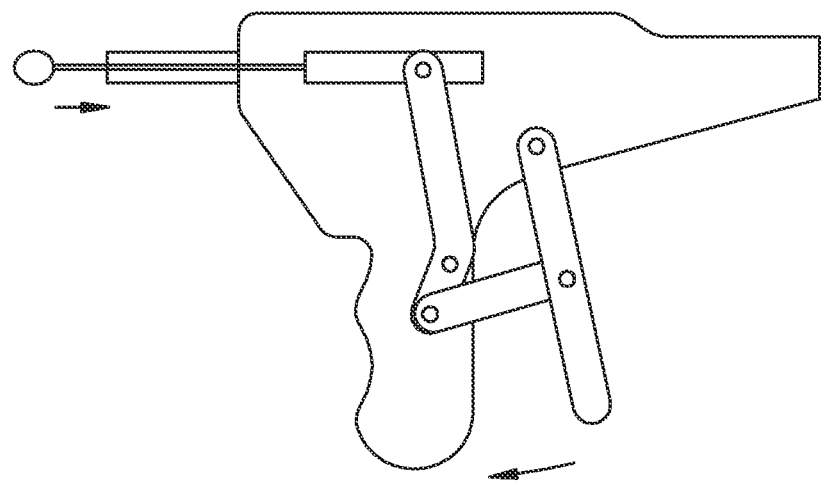
Fig.20
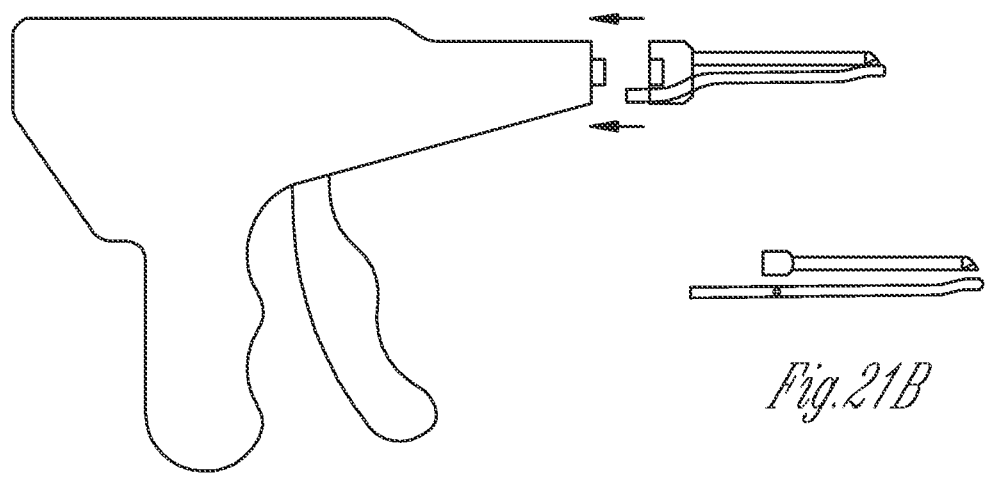
Fig.21A
Fig.21B

FASTENER DEPLOYMENT SYSTEM

CLAIM OF PRIORITY

This application is a division of U.S. application Ser. No. 12/937,361, filed on Oct. 11, 2010 now U.S. Pat. No. 8,387,847, which is the U.S. National Stage Entry of PCT Application PCT/US2009/002235, filed on Apr. 9, 2009. PCT Application PCT/US2009/002235 claims the benefit of priority to U.S. Provisional Application Ser. No. 61/123,807, entitled "FASTENER DEPLOYMENT SYSTEM AND METHOD," filed Apr. 11, 2008. Each of the aforementioned applications is incorporated herein by reference.

BACKGROUND

Nasal septal surgery is a procedure that calls for partial removal of the cartilage and bone dividing the nasal passages. In this procedure, the mucosa is dissected away from both sides of the cartilage and bone, the cartilage is removed, and the mucosa is returned back to the desired location. In addition, the two layers are sutured together in a manner that eliminates air between the layers.

Manual suturing is cumbersome and tedious. During the operation, proper technique must be used to ensure that the sutures do not become too tight and thus leading to localized ischemia. In addition, the operation conducted within a small area requires the surgeon to ensure proper alignment of the septal mucosa tissues.

OVERVIEW

An example of the present subject matter includes a hand-operated fastener delivery device suitable for a surgical application. The device includes a long reach fastener delivery device that ejects a fastener (such as a rivet or a staple) in a direction substantially perpendicular to the axis of reach.

The present subject matter includes various types of fasteners. In various examples, the fastener includes a stud (or rivet) type fastener or a two-legged staple type fastener. One example of a fastener includes a fastener body and a fastener retainer with the fastener body delivered to one side of the work material and the fastener retainer delivered to a second side of the work material. One example includes a blind fastener that is placed and secured in position from a single side of the work material. The fastener can be self-piercing or the fastener can be placed in a hole formed using a separate instrument. In one example, the fasteners include a bioresorbable material.

One example of the present subject matter includes a handle coupled to a first linear member and a second linear member 135. The distal end of the first linear member carries a fastener body to the installation location on a first surface of the work material. The distal end of the second linear member 135 either carries a fastener retainer to a second surface of the work material or provides support for placement and deployment of a blind fastener.

A mechanical linkage of the device translates actuation of the handle into movement of a pushrod. The pushrod moves a fastener body from the proximal end towards the distal end of the first linear member. The distal end of the first linear member terminates in a guide that is configured to re-orient, and eject, the fastener in a direction aligned towards the second linear member 135.

In one example, initial travel of the mechanical linkage causes the distal ends of the first linear member and the second linear member 135 to be drawn together. The distal ends of the first linear member and the second linear member 135 have an unobstructed throat that allows placement of a fastener at a substantial reach distance from an edge of the work material.

Continued actuation of the handle causes the pushrod to eject the fastener with an alignment that is substantially perpendicular to the movement of the fastener relative to the first linear member.

The present subject matter can be used to join the mucosa, fasten tissue, or otherwise close an opening. An example of the present subject matter may reduce the surgical time and improve the accuracy of tissue approximation. Since each fastener is independent of other fasteners or sutures, the possibility of localized ischemia from suture strangulation is reduced. Some examples of the present subject matter are tailored for use during surgery involving the gastrointestinal tract and subcuticular skin.

In addition to applications involving surgical use on soft tissue, other surgical applications or non-surgical applications are also contemplated. An example of the present subject matter can be tailored for use in delivering a fastener to a location having restricted access, such as a deep within a cavity of a structure or a living body.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 4A and 5A illustrate perspective views of engagement of a cam and cam follower.

FIGS. 4B and 5B illustrate overhead views of a device corresponding to engagement of the cam and cam follower.

FIG. 14A includes a device having a rivet cartridge.

FIG. 14B includes a graph illustrating lost motion.

FIG. 20 illustrates a device.

FIG. 21A illustrates a device with detachable linear members.

FIG. 21B illustrates detachable linear members.

DETAILED DESCRIPTION

Figure 1:
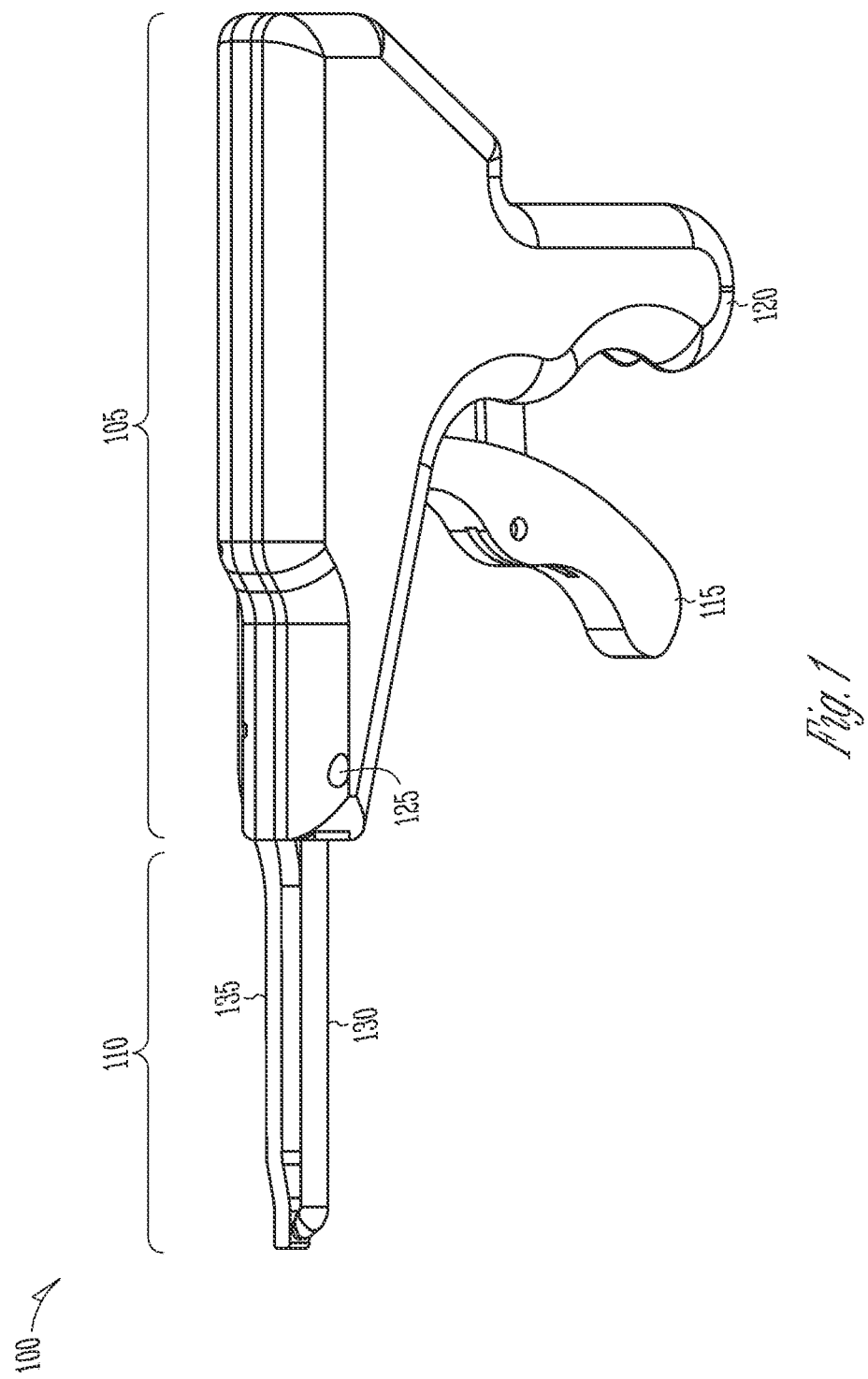
FIG. 1 illustrates a perspective view of a device.

FIG. 1 illustrates a perspective view of device 100. Device 100 includes handle 105 coupled to working portion 110. Handle 105 is user operable and includes a primary hand portion 120 and a secondary hand portion 115. Primary hand portion 120 can be viewed as a ground or a ternary link and secondary hand portion 115 can be viewed as an input in the form of a handle, a lever, or a link. In various examples, the primary hand portion and the secondary hand portion are coupled by a pivot or a mechanical linkage. Handle 105 includes a receiver port 125 configured to accept a fastener. Handle 105, in one example is fabricated of a plastic or other synthetic material.

Working portion 110 includes first linear member 130 and second linear member 135. First linear member 130 is configured to deliver a fastener body. Second linear member 135 is configured to deliver a fastener retainer or configured to provide support for a work material during fastener installation. In the example illustrated, these are fabricated of a metal having rectangular or circular cross sections.

Figure 2:
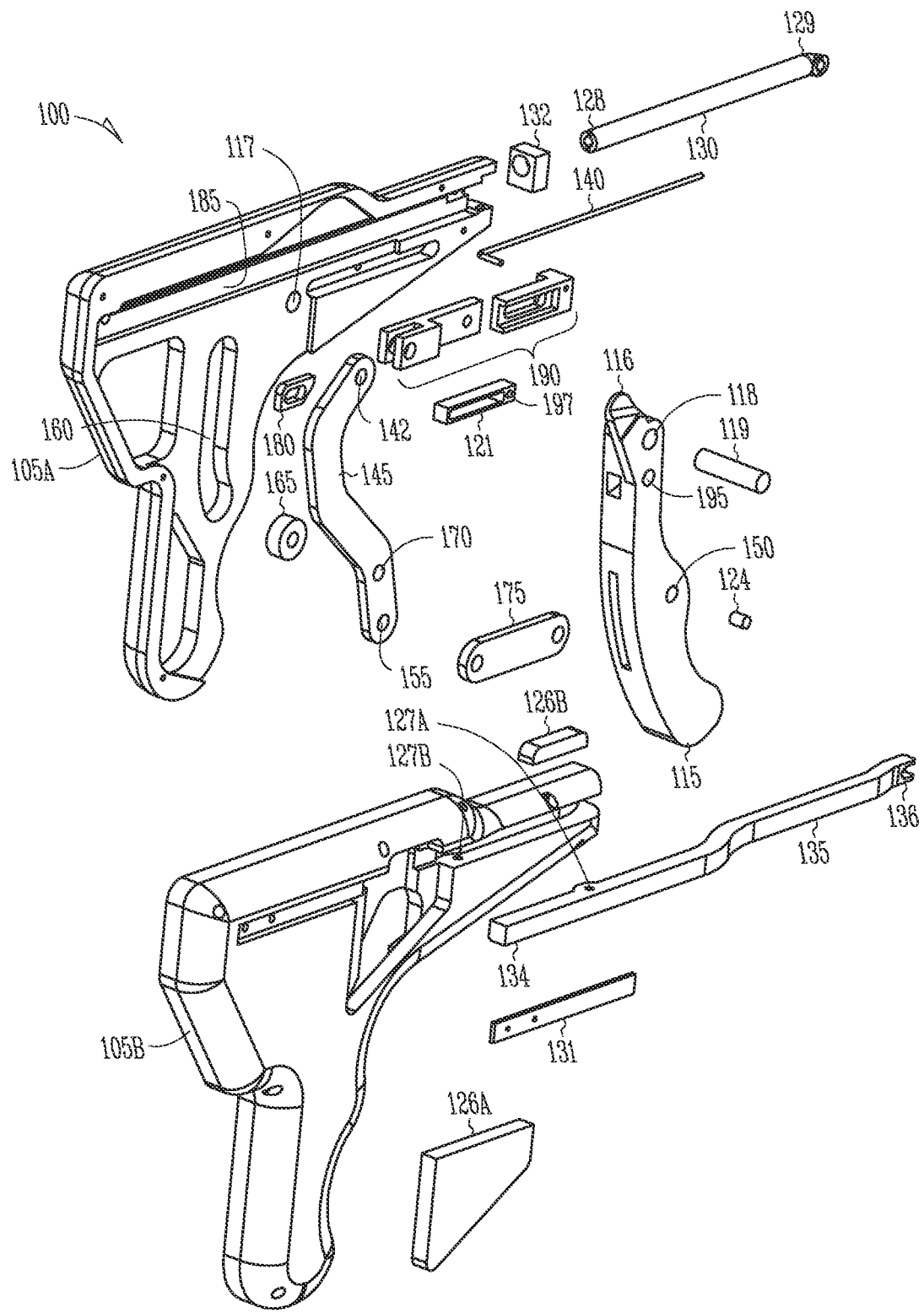
FIG. 2 illustrates an exploded view of a device.

FIG. 2 illustrates an exploded view of device 100. Handle 105A and handle 105B denote the left and right, respective, sides of handle 105. Secondary hand portion 115 is coupled to handle 105 by a mechanical linkage including, among other things, binary link 175 and ternary link 145. By the mechanical linkage, secondary hand portion 115 is also coupled to fastener driver 140. Fastener driver 140, in the example illustrated, includes a pushrod or shaft that operates within a channel of first linear member 130. In one example, fastener driver 140 includes a flexible end portion that follows the interior contours of the channel of the first linear member 130. Secondary hand portion 115 includes cam 116 at one end. Cam 116 includes a shaped surface that engages a complementary shaped surface of proximate end 134 of second linear member 135. Bore 117 in primary hand portion in handle portion 105A receives pin 119. Pin 119 also passes through bore 118 in secondary handle portion 115. Bore 195 in secondary handle portion 115 is coupled to spring 196 (shown in FIG. 3). Block 121 includes bore 197. In one example, block 121 is repositionable to adjust tension applied by spring 196 coupled to bore 197. Pin 124 is located in bore 150 of secondary handle portion 115 and is coupled to link 175. Cover structure 126A and cover structure 126B conceal openings in handle portion 105A and 105B.

In various examples, fastener driver 140 includes a push cable, a ribbon or other structure that functions in the manner described.

The mechanical linkage of one example of the present subject matter provides approximately four inches of linear travel in response to approximately 30 degrees of handle actuation. Other dimensions are also contemplated. The mechanical linkage of the present subject matter provides tactile feedback to the operator during fastener deployment.

First linear member 130 includes distal end 129 and proximate end 128. In the example illustrated, first linear member 130 includes an internal channel or lumen that carries a fastener body in an alignment whereby a longitudinal axis of a linear stud of a rivet type fastener is aligned with an axis of the internal channel. Distal end 129 is configured to re-align the fastener to eject the fastener in a direction substantially perpendicular to the axis of the internal channel. First linear member 130 is affixed to handle 105 by mounting block 132. First linear member 130 is illustrated as having a circular cross section, however other configurations are also contemplated.

Second linear member 135 is coupled to handle 105 by a pivot joint aligned on bore 127A (near proximal end 134 of second linear member 135) and by bore 127B of handle 105. Leaf spring 131 is affixed to handle 105 and exerts a force on proximal end 135 to normally hold distal end 136 apart from distal end 129 of first linear member 130. Leaf spring 131 can be viewed as a hold open spring. Second linear member 135 is configured as a rectangular cross section, however, other configurations are also contemplated. In the figure, second linear member 135 has offset portions that are configured to position distal end 136 for nasal septal surgery.

In one example, working portion 110 (including first linear member 130 and second linear member 135) has a relatively high aspect ratio. The aspect ratio can be viewed as the length divided by width. In particular, length can refer to the length of either linear member and the width is measured perpendicular to the length. Aspect ratio can refer to a length of the linear member relative to a diameter of that same linear member, relative to a cross-sectional dimension of that same linear member, or relative to an overall width dimension measured across both the first linear member 130 and the second linear member 135.

A device having a high aspect ratio may be suitable for use in a deep cavity having a small orifice. The aspect ratio can be described as a ratio of a length and a width. In the present subject matter, the length can be viewed as the overall length of either linear member 130 or linear member 135 (as measured in parallel with axis 335 of FIG. 11), and the width can be viewed as a width over both linear member 130 and linear member 135 (as measured in parallel with axis 330 of FIG. 11). The present subject matter can be configured as a tool having a high aspect ratio of, for example, greater than 2, however, the aspect ratio can also be smaller.

With a high aspect ratio, the present subject matter enables delivery of fasteners at a position that is remote from the hand portion. The fastener can be stored in a magazine coupled to the device or manually loaded at a location near the hand portion. As such, the fastener is carried to the installation site without having to remove the device from, for example, a body cavity. In addition, the present subject matter operates using a push rod or similar system that provides haptic feedback to the operator. A ratcheting system, on the other hand, is not able to provide haptic feedback and thus, lacks sensitivity.

Relative motion between primary hand portion 120 and secondary hand portion 115 is translated, by the mechanical linkage, to linear movement of fastener driver 140 and to angular movement of second linear member 135. Secondary hand portion 115 is coupled to binary link 175 at bore 150. Binary link 175 is also coupled to ternary link 145 at pivot 155. Pivot 170 of ternary link 145 is coupled to bearing 165. Bearing 165 is free to rotate on the axis of pivot 170 and engages with cam slot 160 of left side handle 105A. Ternary link 145 is also coupled to sliding link 180 at pivot 142. Sliding link 180, in the example illustrated, is configured as a t-nut that engages slot 185 of left side handle 105A. Pivot 142 also is coupled to fastener driver 140 by link 190. Movement of the handle causes the t-nut to slide in slot 185 with forward (or advancing) motion when squeezed together and rearward (or retraction) motion when released. A sliding joint is sometimes referred to as a prismatic joint. A prismatic joint allows a single-axis sliding function.

Figure 3:
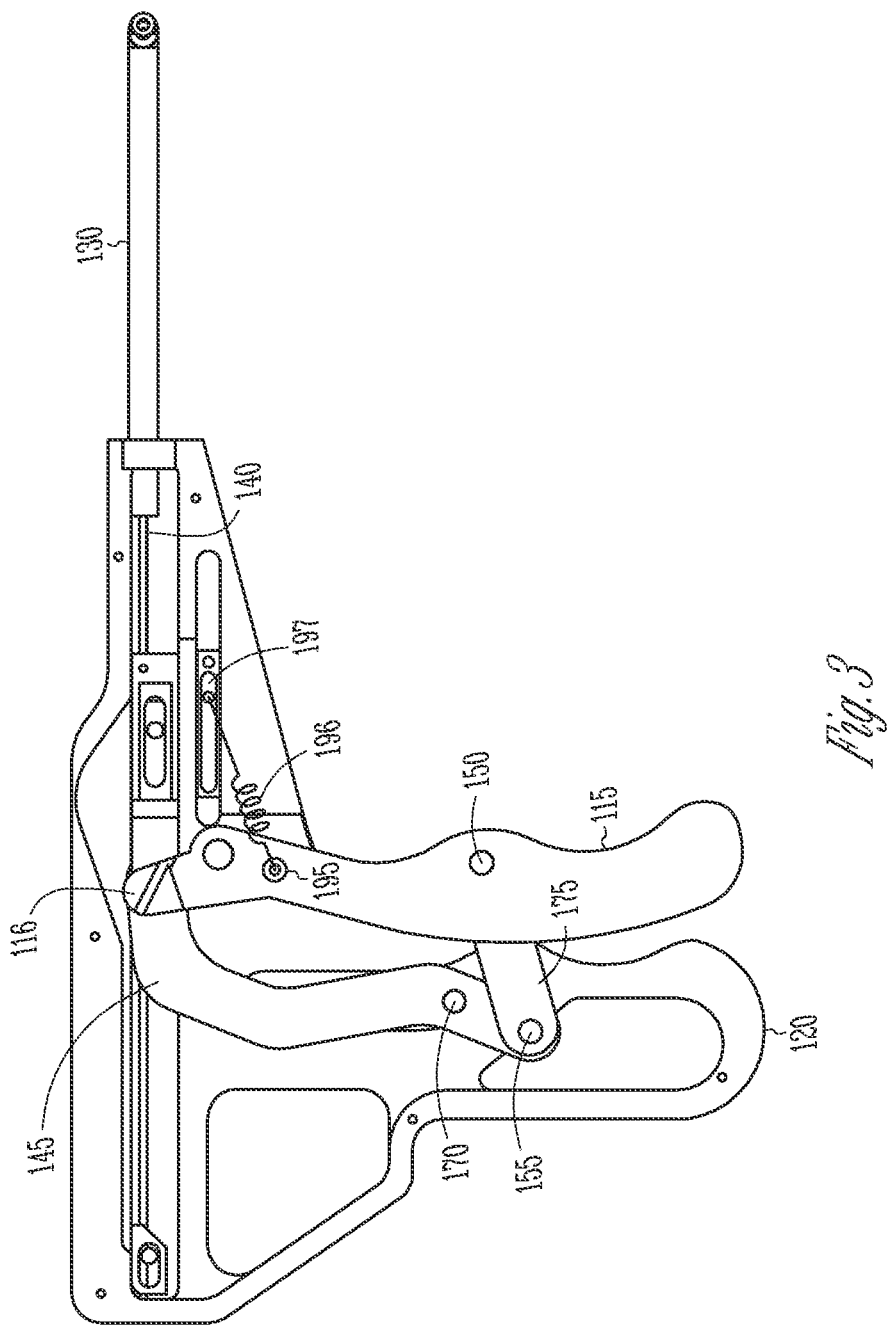
FIG. 3 illustrates a view of a partially assembled device.

FIG. 3 illustrates a view of a partially assembled device. The figure depicts relative orientation of primary hand portion 120, secondary hand portion 115, binary link 175, ternary link 145, fastener driver 140, and first linear member 130. A first end of extension spring 196 is affixed to handle 105A at anchor 197 and a second end is affixed to point 195 on secondary hand portion 115. Spring 196 exerts a force to return secondary hand portion 115 to a position distal from primary hand portion 120. In addition, and by virtue of the mechanical linkage, spring 196 also exerts a force to retract fastener driver 140 and to return cam 116 to a position that allows second linear member 135 (not shown in this figure) to return to an open position relative to first linear member 130.

Figure 4A:
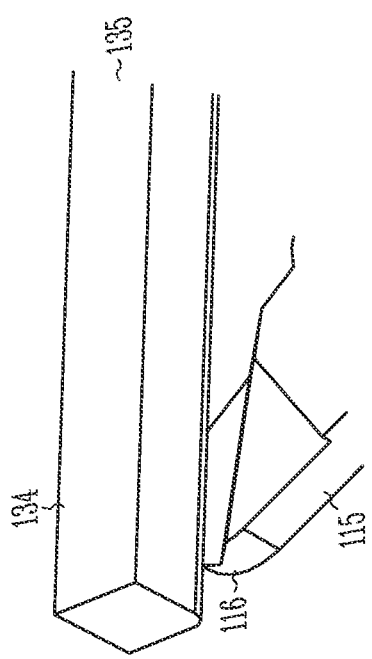
Figure 4B:
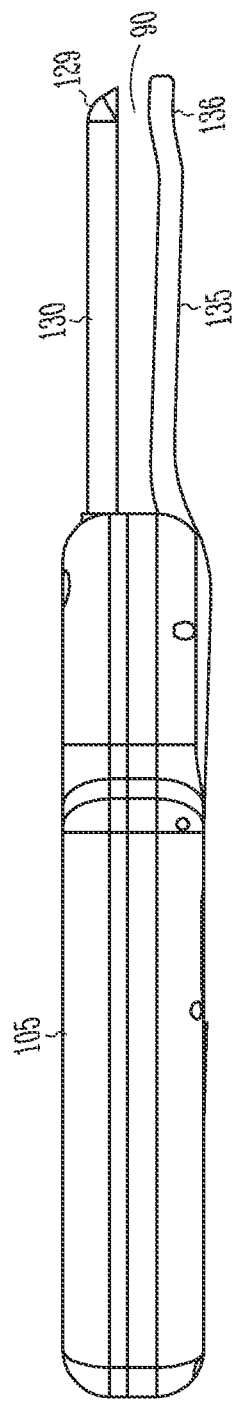

FIGS. 4A and 5A illustrate perspective views of engagement of a cam and cam follower. In FIG. 4A, cam 116 is at a position near proximate end 134 (of second linear member 135). In the position shown, first linear member 130 and second linear member 135 have distal ends 129 and 136 that are spaced a linear distance apart, as shown in FIG. 4B. Throat 90 refers to the unobstructed opening between first linear member 130 and second linear member 135. The present device can place a fastener at a distance from an edge of a work material that is equal to the length of the throat, a dimension sometimes referred to as the reach. The reach is thus, the distance between distal end 129 (or distal end 136) and the point of attachment to handle 105. In one example of the present subject matter, the reach is approximately four inches.

In FIG. 5A, cam 116 is in slidable contact with proximate end 134 (of second linear member 135). In the position shown, first linear member 130 and second linear member 135 have distal ends 129 and 136 that are drawn together, as shown in FIG. 5B. Second linear member 135 pivots on a pin (not shown) passing through bore 127A.

Figure 11:
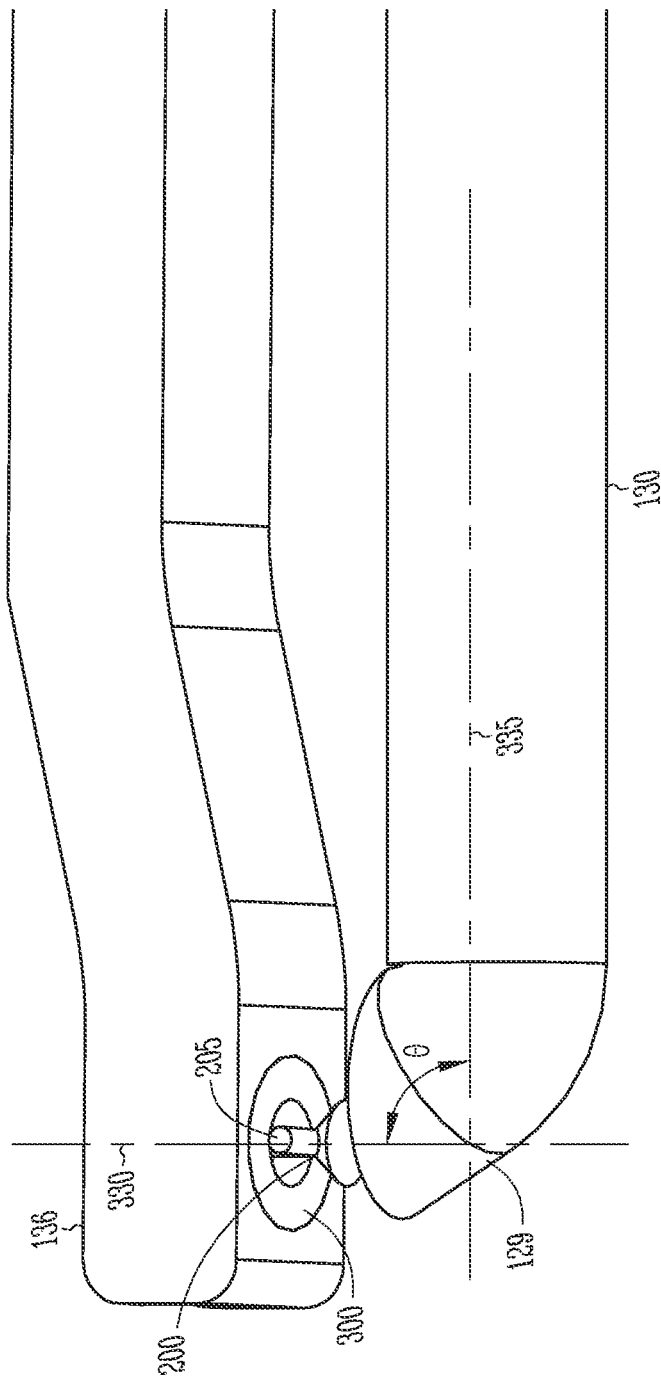

In addition to the cam and cam follower illustrated in the figures, other structures can be used to control a position of one linear member relative to the other linear member. For example, a position controller can include a gear, a spring, or a catch or other structure that adjusts a linear distance between the distal end of first linear member 130 and the distal end of second linear member 135. The linear distance can be measured perpendicular to a longitudinal axis of the device. FIG. 11 illustrates longitudinal axis 335.

Figure 6:
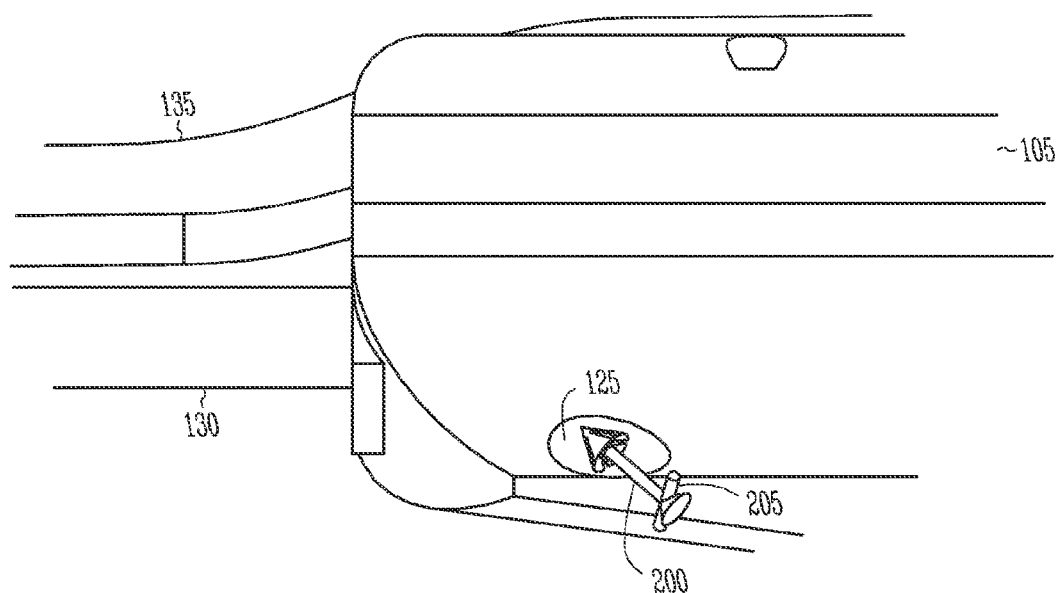
FIGS. 6 and 7 illustrate introduction of a fastener into a channel.
Figure 7:
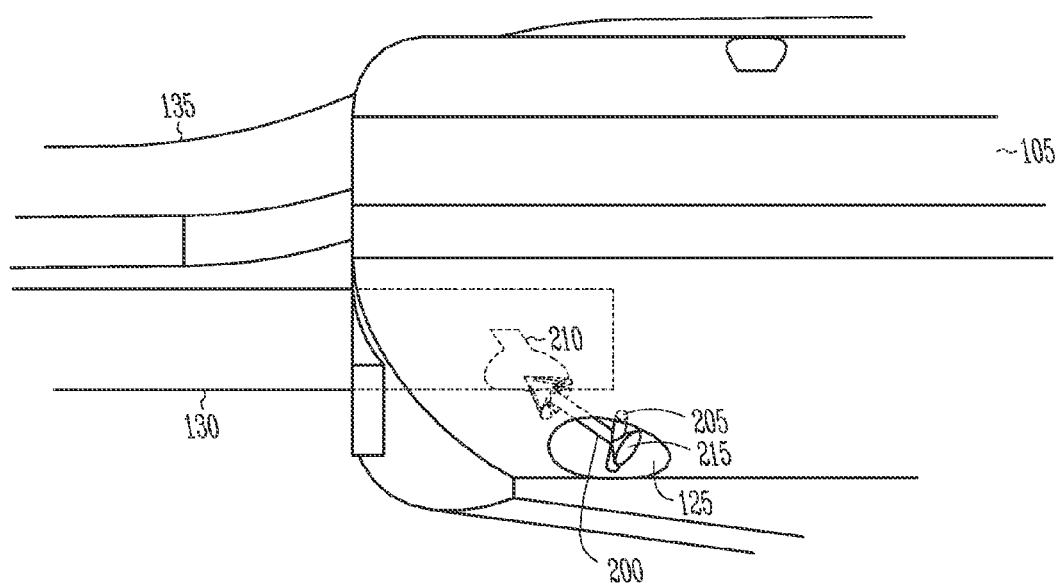

FIGS. 6 and 7 illustrate introduction of fastener 200 into a channel in communication with first linear member 130. In the figures, receiver port 125, in handle 105, is illustrated as an opening having a round or oval shape and is configured for use with a fastener having a single stud similar to that of a rivet. Fastener 200, as illustrated, includes cross-member 205 under the head that serves to index the fastener within the interior channel of first linear member 130. FIG. 7 illustrates a port in first linear member 130 having rectangular keyway 210. Rectangular keyway 210 is configured to engage cross-member 205 of fastener 200. Fastener 200 also includes a head having concave or conical feature 215. Conical feature 215 is configured to engage with an end of fastener driver 140.

Figure 8:
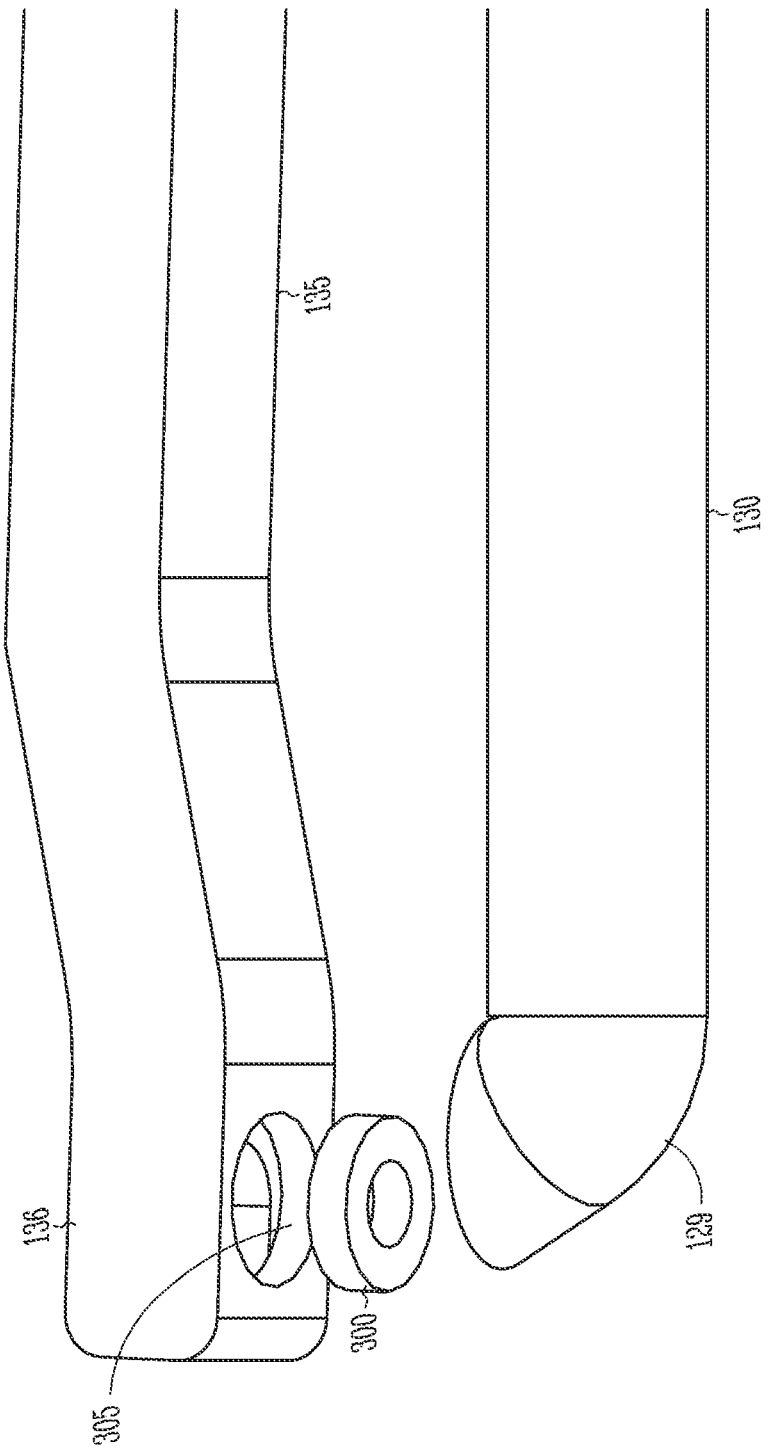
FIGS. 8 and 9 illustrate a fastener retainer.
Figure 9:
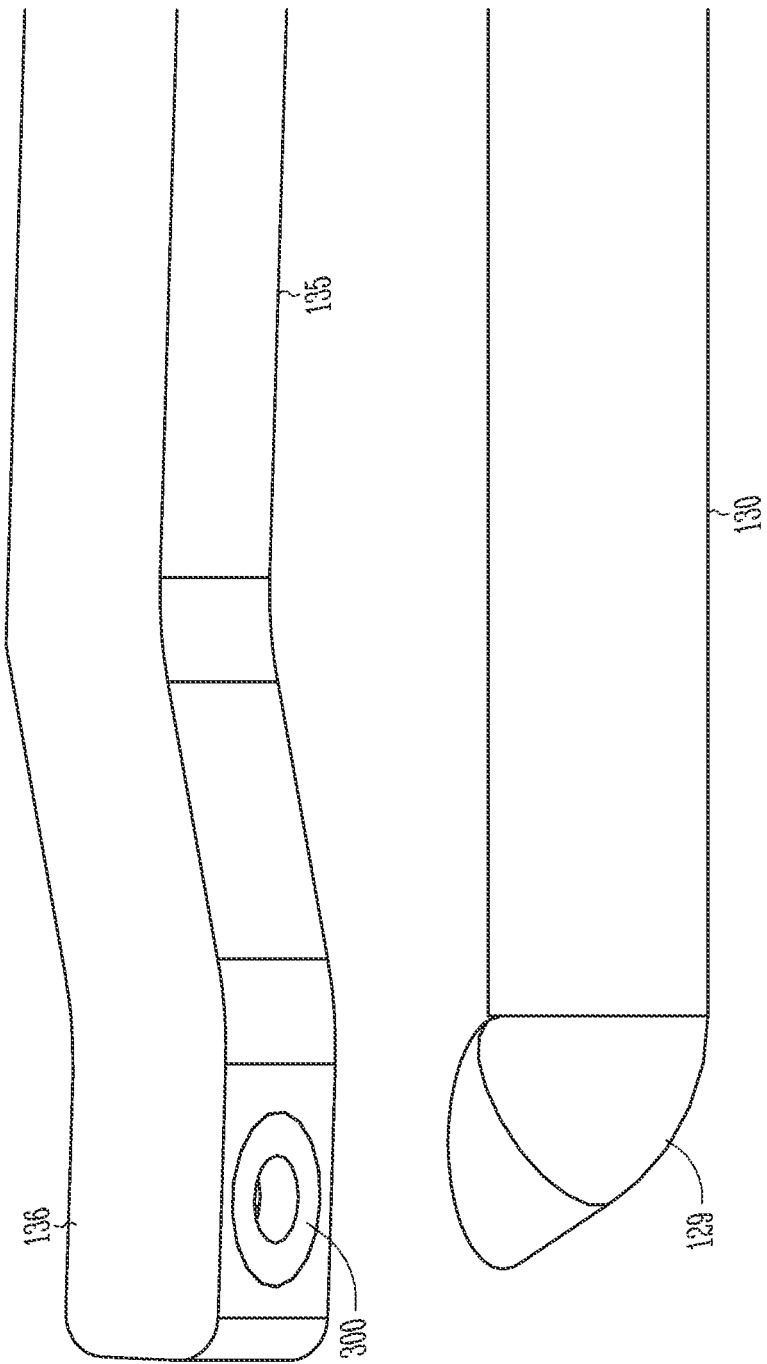

FIGS. 8 and 9 illustrate fastener retainer 300. In FIG. 8, fastener retainer 300 is illustrated as a ring having an internal diameter configured to receive fastener 200. The outside diameter of fastener retainer 300 is configured to distribute a compressive load over a portion of the tissue or other work material. Distal end 136 of second linear member 135 includes opening 305 configured to receive fastener retainer 300, as shown in FIG. 8 and FIG. 9. In the example shown in the figure, a structure of distal end 136 holds retainer 300 in a position flush with the surface of the second linear member 135. Distal end 129 of first linear member 130 is included to illustrate relative alignment as to second linear member 135. Other types of fastener retainers, or cleats, are also contemplated.

Figure 10:
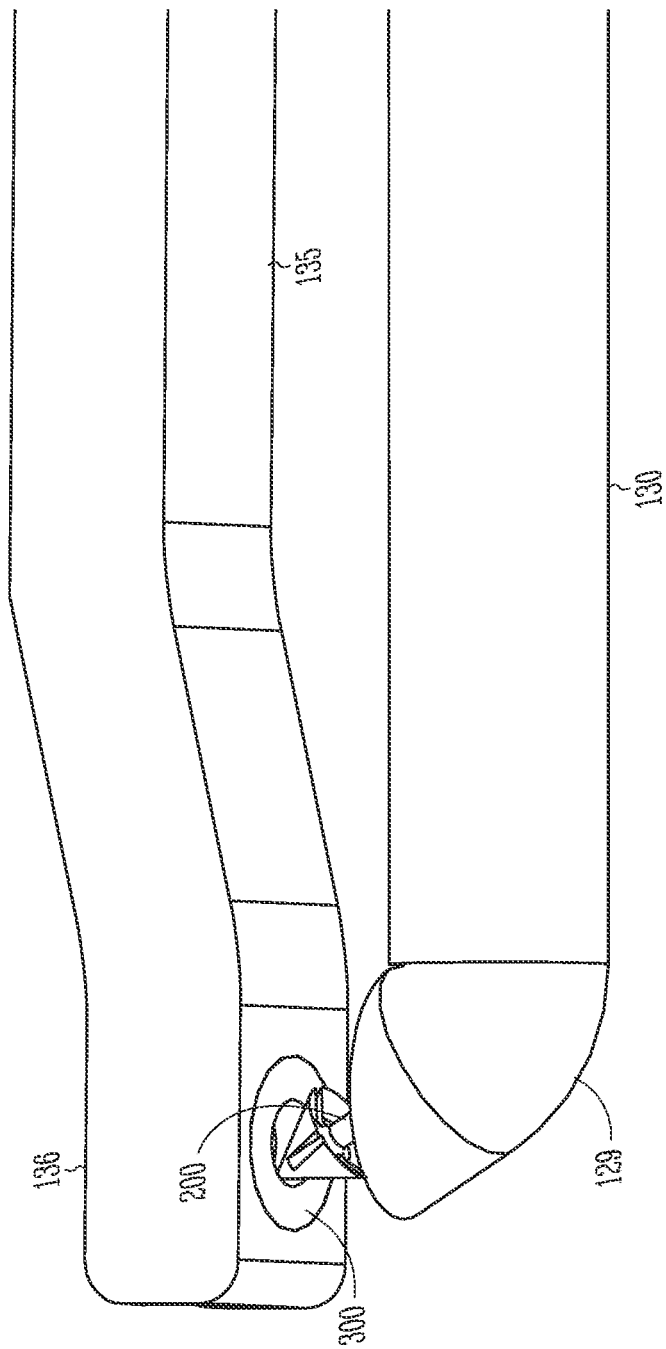
FIGS. 10 and 11 illustrate engagement of a fastener and a fastener retainer.

FIGS. 10 and 11 illustrate engagement of fastener 200 and fastener retainer 300. In FIG. 10, fastener 200 is not yet fully ejected from distal end 129 of first linear member 130 and not yet fully engaged with fastener retainer 300. In both figures, fastener retainer 300 remains coupled to distal end 136 of second linear member 135. Fastener 200 includes a conical end or barb configured to pass through, and lock onto, the internal diameter of fastener retainer 300. In FIG. 11, the conical end of fastener 200 is not visible, as it has passed through the internal diameter of fastener retainer 300.

In FIG. 11, longitudinal axis 330 of fastener 200 and longitudinal axis 335 of first linear member 130 are shown. Axis 330 and axis 335 are at approximately 90 degrees, or substantially perpendicular, as denoted by angle φ. While fastener 200 is carried within the channel of first linear member 130, axis 330 and axis 335 are essentially collinear, or parallel. In the figure, a structure within the channel of distal end 129 engages with cross-member 205 to maintain alignment of fastener 200 during ejection.

Figure 12:
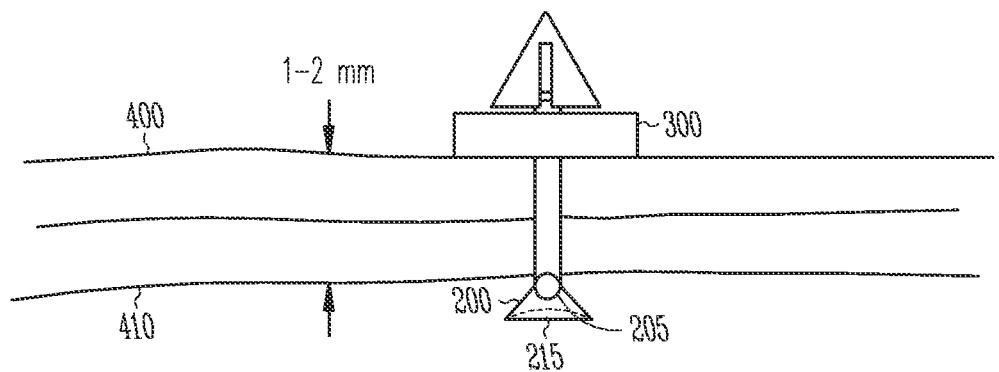
FIG. 12 illustrates a fastener and a fastener retainer.

FIG. 12 illustrates fastener 200 and fastener retainer 300 affixed to work material 400 and work material 410. Work material 400 and work material 410 can include tissue, graft material, or other substance to be joined. In one example, the thickness of the work material stack is approximately 1 to 2 mm.

Fastener 200 includes a barbed or conical end having multiple segments that allow engagement with fastener retainer 300. A surface of fastener retainer 300, as illustrated, lies in contact with a first surface of the work material. A second surface of the work material lies in contact with the head of fastener 200. Cross-member 205 is disposed near the head of fastener 200. The head includes an internal (or concave) conical feature 215 configured to receive fastener driver 140. In various examples, the fastener end, or the fastener retainer includes separate segments or other structure to allow the fastener to engage in a one-way lock configuration with the fastener retainer.

Figure 13A:
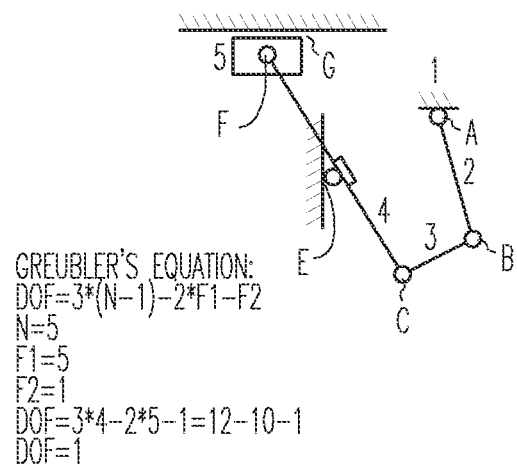
FIGS. 13A, 13B, 13C and 13D illustrate kinematic diagrams for a mechanical linkage.
Figure 13B:
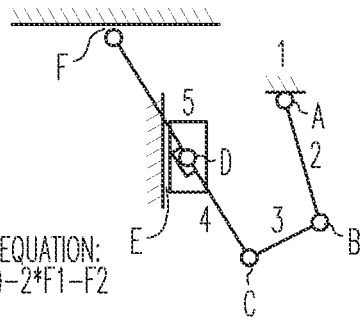
Figure 13C:
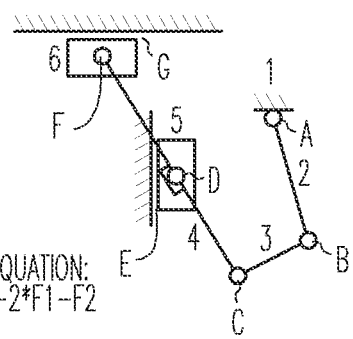
Figure 13D:
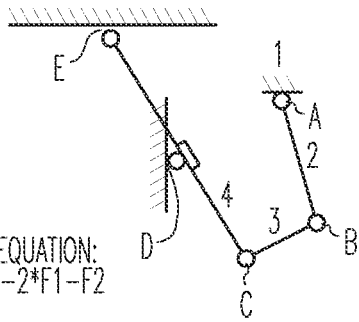

FIGS. 13A, 13B, 13C and 13D illustrate kinematic diagrams for a mechanical linkage having one degree of freedom. FIGS. 13A, 13B, 13C and 13D show, in various combinations, link 1, link 2, link 3, link 4, and link 5, and link 6 and joint A, joint B, joint C, joint D, joint E, joint F, and joint G. Fixed links are denoted with crosshatching and revolute joints are denoted with circles. FIG. 13A shows a five-bar, two-slider design corresponding to an example of a structure illustrated elsewhere in this document. FIG. 13B shows an alternate configuration of a five-bar design. FIG. 13C illustrates a six-bar design and FIG. 13D illustrates a four-bar design.

FIG. 13C corresponds to the example shown in FIG. 2. For example, the base structure, or ground, is denoted in FIG. 13C by the cross hatching at point A, point E, and point G. The base structure corresponds to handle 105A and 105B in FIG. 2. Link 2 in FIG. 13C corresponds to the input denoted as handle 115 in FIG. 2. Binary link 3 in FIG. 13C corresponds to binary link 175 in FIG. 2. Ternary link 4 in FIG. 13C corresponds to ternary link 145 in FIG. 2. Sliding joint 5 in FIG. 13C corresponds to the pin in slot joint of FIG. 2 formed by bearing 165 in slot 160. Sliding joint 6 in FIG. 13C corresponds to the prismatic joint of FIG. 2 in which driver 140 travels. In the examples shown, approximately 30 degrees of rotation of the input corresponds to approximately four inches of linear travel.

Method of Manufacturing

The present subject matter can be fabricated using various combinations of metal or plastic components. In one example, the handle includes a lightweight plastic and the first and second linear members are each fabricated of stainless steel. The various components are provided and assembled in the manner illustrated and described herein.

Method of Use

The present subject matter can be used for surgical applications. In the case of nasal septal surgery, the first linear member 130 and second linear member 135 are inserted in the respective nostrils of a patient. The side discharge ejection of the fastener allows an operator to manipulate the hand portions to drive a fastener from the proximate end of the first linear member 130 to the distal end, pierce the tissue, and engage the fastener retainer.

In one example, the first linear member 130 and the second linear member 135 are drawn together with a first portion of the cycling of the handle. With continued actuation of the user operable handle, the fastener is moved from the proximate end to the distal end of the first linear member 130. With yet further continued action of the user operable handle, the fastener turns the corner at the distal end of the channel and is ejected from the first linear member 130. In moving the fastener from the first linear member 130, the fastener also pierces the work material and engages the fastener retainer held in alignment by the distal end of the second linear member 135.

Upon release of the actuation force on the handle, return spring 196 withdraws the fastener driver from the distal end of the first linear member 130 and, in overcoming the force of leaf spring 131, returns second linear member 135 to an open position relative to first linear member 130. In addition, one example provides that the fastener retainer is released from the second linear member 135 and is held captive by the fastener body.

Additional Examples

In one example, an array of fasteners are connected to a carrier or held in a magazine. A spring or other action (such as manipulation of the handle) exerts a force to advance a fastener into the proximate end of the first linear member 130. The device (including the handle and the linear members) is configured for sterilization to allow repeated usage. The array of fasteners is provided in an assembly that can be readily engaged with the device and removed when depleted, to allow an unlimited number of fastener installations in a single surgical application.

In one example, an array of fastener retainers is held in a carrier or other magazine.

Fastener 200 is shown as having a rivet-style configuration. Various types of fasteners are also contemplated including a two-legged staple type, blind fastener, single piece, and multiple piece.

For use with a blind fastener, the device is configured to deliver a fastener using the first linear member 130 and the second linear member 135 serves to support, or buck, the insertion of the fastener from the one side. As such, no portion of the fastener is delivered using the second linear member 135. The distal end of the second linear member 135, in one example, includes one or more clearance holes to allow passage of the fastener through the work material.

For use with a fastener that uses a fastener retainer, the second linear member 135 can be configured to deliver a single fastener retainer or configured to deliver a series of fastener retainers in conjunction with the delivery of each individual fastener.

Various types of rivet-style fasteners are contemplated. For example, the shaft of the fastener can have a barbed or ribbed surface or a series of beaded elements that provide a clamping force when deployed.

One example of a blind fastener includes a hollow shaft with a center mandrel. An insertion force applied to the end of the mandrel exerts a splaying force to enlarge the blind side of the fastener. One example of a blind fastener includes a pivoting toggle portion that can be positioned to readily pass through (or pierce) the work material and when clear of the work material on the blind side, take a position that precludes removal of the fastener. One example of a blind fastener includes a ribbed or barbed shank that is retained by a ring-type fastener retainer or the work material itself.

Various types of staple-style fasteners are also contemplated. For example, the fastener can be deflected or deformed to cinch the work material or a fastener retainer can be installed that engages with a feature of the legs of the fastener. A linkage coupled to the fastener driver can be configured to cinch the legs of the fastener.

In one example, the fastener retainer includes a filled globule. The filled globule can include, for example, an adhesive filled reservoir. On placement and deployment of the fastener, the globule is ruptured by a leg or stud of the fastener and an adhesive or other material is released. The globule then binds the fastener and maintains the compressive force on the work material.

The fastener (along with any fastener retainer), can be fabricated of a variety of materials. In one example, the fastener is fabricated of a biocompatible or a bioresorbable material. An example of a bioresorbable material can dissolve in a biological environment over a time of approximately 7-10 days. One example of a biocompatible material includes a poly-lactic acid/poly-glycolic acid (PLA/PGA) co-polymer. Such a polymer degrades via a process of hydrolysis and is gradually absorbed by the body over a period of time.

In one example, the second linear member 135 carries a plurality of fastener retainers. The plurality of fasteners are arranged in a serial configuration within a channel of the second linear member 135 and are individually advanced as fasteners are deployed. A fastener retainer driver mechanism incrementally moves the fastener retainers into position for engagement.

In one example, the distal end of the first linear member 130 includes a structure that brings the axis of the fastener relative to the axis of the first linear member 130 to an angle of less than 90 degrees. In this case, the fastener can be configured to have an asymmetrical profile that engages with the fastener retainer and pulls the axis of the fastener into a near 90-degree position. With an asymmetrical profile, the fastener is held in relative alignment within the channel of the first linear member 130 by an indexing structure. An example of an asymmetrical profile includes a curved end. An example of an indexing structure includes the cross-member described elsewhere in this document.

In one example, fastener driver 140 includes an end configured to seat with and engage the head of the fastener. For example, with a conical feature in the fastener head, the end of fastener driver 140 can be a similarly shaped cone or rounded structure.

In one example, the distal end of the first linear member 130 and the distal end of the second linear member 135 are drawn together with the first small movement of the handle by the user. In various examples, either one or both of the first linear member 130 and the second linear member 135 are re-positionable by operation of the handle. In one example, both linear members remain stationary and the linear distance there between is configured for using in a particular application. In other words, either one or both of the first linear member 130 and the second linear member 135 are stationary or movable. In one example, the linear member is pivotally coupled to the handle, however other types of movement are also contemplated.

In one example, a portion of the fastener is configured to form a piercing hole coincident with deployment of the fastener. In one example, a fastener is deployed in a pre-formed hole. A feature affixed to either the first linear member 130 or the second linear member 135 facilitates alignment with the preformed hole.

In one example, the fastener is delivered by conveyance through a lumen or channel of the first linear member 130. In one example the first linear member 130 includes a track or other channel structure and the fastener travels to the distal end by a corresponding feature that engages a surface of the track or channel.

Other types or configurations of springs, mechanical linkages, or other structures are also contemplated. For example, rather than strictly linear, the linear members described herein can have a curvature that facilitates placement and deployment of a fastener.

In one example, the first linear member 130 and the second linear member 135 are configured as two parallel tubes. In one example, the first linear member 130 and the second linear member 135 are configured as tubes having an arbitrary (for example, curved or arched) shape. The ends of the first linear member 130 and the second linear member 135 can be generally parallel. The configuration of the first linear member 130 and the second linear member 135 can be tailored to specific patient anatomy or to another purpose not necessarily related to medical care.

The cross-sectional shape of the first linear member 130 and the second linear member 135 can be of various configurations. For example, the linear members can be tubular, rectangular, very flat, a channel, a guide, T-slot, or other configurations.

In one example, the first linear member 130 and the second linear member 135 are fabricated of a shape memory material. A shape memory material is able to change from one shape to another when deployed or during deployment. In addition, other structure of the device (for example, the fastener driver) is configured to accommodate different curvatures of the linear members over a large range of radiuses and provided that minimum bend radius of the cable or ribbon used for the fastener driver is not exceeded.

In one example, the first linear member 130 and the second linear member 135 are configured for field-replacement and as such, a user can select and install a particular linear member according to a particular application. The hand piece is configured to receive the various linear members. The various linear members can have different configurations, shapes, lengths and cross sections. In this example, the linear members are disposable items and the hand piece can be sterilized for later use.

FIG. 14A includes device 105 having rivet cartridge 1410. Rivet cartridge 1410 is illustrated as having a spool design in which individual rivets are coupled to a coiled carrier strip. An aperture in a surface of device 105 receives the rivets of cartridge 1410. In the figure, actuator rod 1405 appears extending from linear member 1400. Linear member 1400 and actuator rod 1405 can be rigid or flexible. An exposed portion of actuator rod 1405 has length L and is controlled by actuation of pivot mounted handle 1407. Handle 1407 sweeps through angle $\theta$ which carries actuator rod 1405 through length L.

FIG. 14B includes a graph illustrating lost motion. The abscissa includes angle $\theta$ (degrees) and the ordinate includes length L (inches). In one example, a linear relationship exists between angle $\theta$ and length L, however, a non-linear relationship can also be provided based on adjustment of dimensions and re-configuration of selected links and joints. As shown, approximately 30 degrees of rotation corresponds with linear travel of approximately four inches.

Regions 1420, 1430, 1440, and 1450 correspond with different portions of travel of handle 1407. Each of regions 1420, 1430, 1440, and 1450 can be correlated to a specific function performed by the device. For example, at region 1420, a rivet can be advanced in a linear member by approximately two inches, at region 1430, a compressive force is applied to the working tissue, at region 1440, a rivet body is ejected and at region 1450, a piercing force and an upsetting force is applied to secure the rivet body and washer. Other combinations of sequential or parallel functions can also be provided with various examples.

In one example, a first range of motion causes a rivet to be carried for a distance of 2" of linear travel, and a second range of motion causes a washer to move 2".

In one example, the first 3" of travel is used to push a rivet through a linear member, the next 0.5" of travel is used to push a washer into position, and the last 0.5" of travel is used to advance both the rivet and the washer together.

In one example, a first 3" is used to grasp and pull tissue into a device, and the last 1" of travel is used to fix tissue together. This can be used for NOTES (natural orifice transluminal endoscopic surgery) style surgery or laparoscopic procedures.

In one example, a single actuation causes sufficient linear travel to provide grasping of tissue (pull towards or push away from), making an incision, placing an object through the incision, and closing the incision.

Various tools and implements can be affixed to the device of the present subject matter. For example, actuator rod 1405 can be used to operate a saw, provide therapy, cleaning, create frictional heat or navigate an instrument through a curved pathway. For example, with a suitable end instrument, a snare or other grasping function can be performed by an example of the present subject matter.

Figure 15A:
FIGS. 15A, 15B, and 15C illustrate views of a rivet cartridge.
Figure 15B:
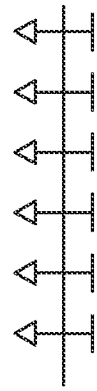
Figure 15C:
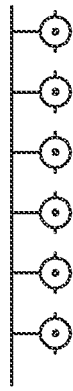

FIGS. 15A, 15C, and 15D illustrate top, side, and frontal views, respectively, of a rivet cartridge according to one example. In the figure, individual rivets are carried on a strip of material such as plastic or light metal.

Figure 16:
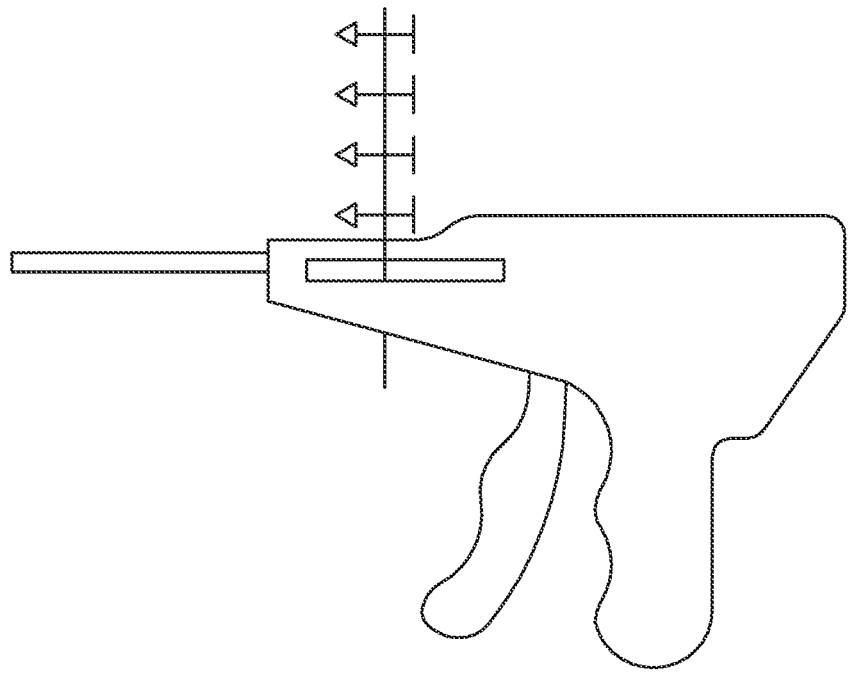
FIG. 16 illustrates a device having a rivet cartridge.

FIG. 16 illustrates a device having a rivet cartridge. In the figure, the rivet cartridge feeds in a downward direction. Unused rivets are visible above the device and spent rivets are absent from the carrier strip visible beneath the device.

Figure 17A:
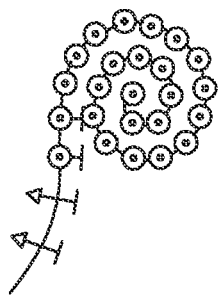
FIG. 17A illustrates a rivet cartridge.
Figure 17B:
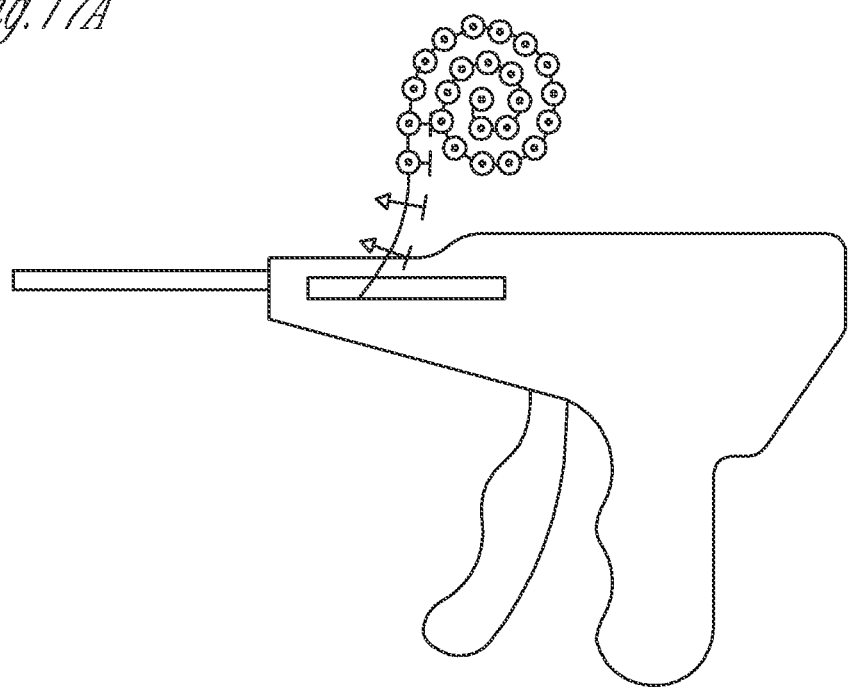
FIG. 17B includes a device having a rivet cartridge.

FIG. 17A illustrates a rivet cartridge having a spiral configuration. The individual rivets are affixed to a carrier strip and shown coiled. FIG. 17B illustrates a device having a spiral-shaped rivet cartridge.

Figure 18A:
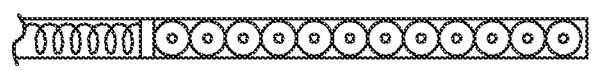
FIGS. 18A and 18B illustrate linear members.
Figure 18B:
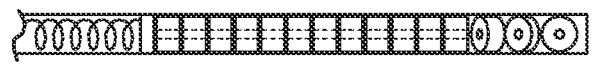

FIGS. 18A and 18B illustrate examples of linear members. In both figures, individual washers are shown within a sectional view of a linear member. The washers are used in conjunction with the rivet bodies described elsewhere in this document. The washers are advanced under pressure applied by an internal spring. The individual washers are arranged in a planar arrangement in FIG. 18A and in a stacked arrangement in FIG. 18B.

Figure 19A:
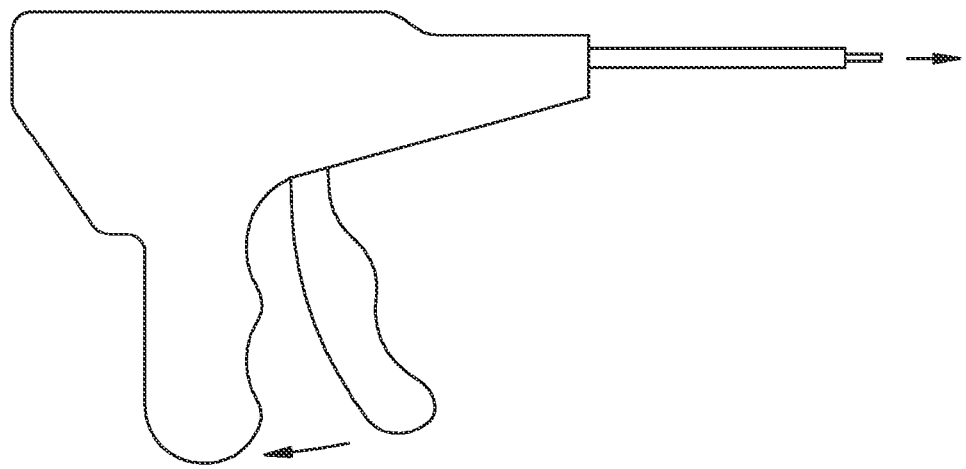
FIGS. 19A and 19B illustrate a device.
Figure 19B:
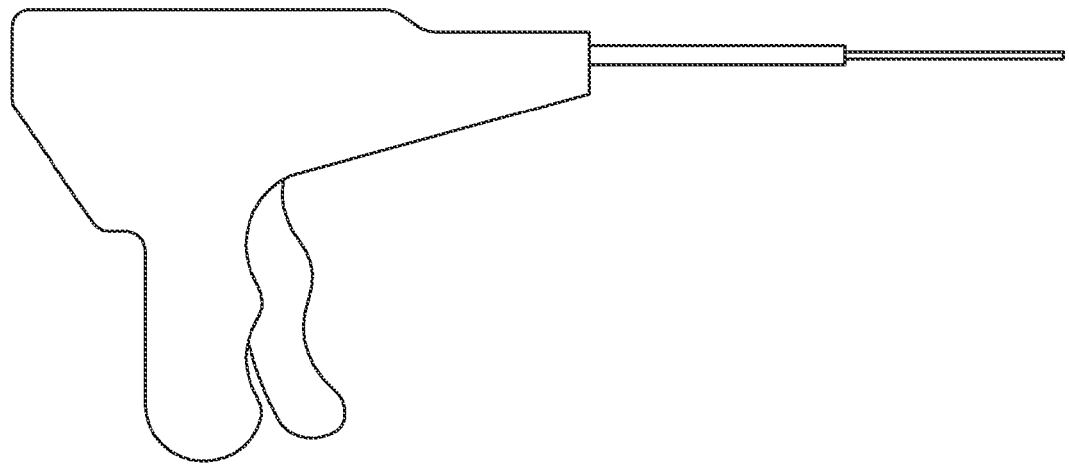

FIGS. 19A and 19B illustrate a device in which the linear travel occurs within the linear member and the actuator rod extends or retracts when the handle is manipulated. For example, a cautery tool, a snare device, a forceps, a clamp, or a suturing tool can be affixed to the actuator rod and manipulated to perform a surgical (or non-surgical) operation. The linear members can be flexible or rigid. FIG. 19A illustrates extension of the actuator rod when the handle is squeezed in a direction towards the base structure and FIG. 19B illustrates the actuator rod in a fully extended position.

FIG. 20 illustrates a device in which the input lever and the actuator rod are located on opposing sides of the primary handle portion of the base structure. In this example, actuation of the input lever in a direction of squeezing relative to the primary handle portion causes the actuator rod to retract into the linear member. This configuration can be used for pulling tissue or a work piece in a direction towards the device. For example, traction/counter-traction, reaching and deep tissue pulling can be performed using the device shown. In one example, the device is configured for a colostomy operation or for retrieving a portion of an intestine. A locking feature can be added to fix a position of the actuator rod in order to retain an organ or other tissue in a selected position.

FIG. 21A illustrates a device with detachable linear members. The linear members can be removed and replaced. For example, the linear members can be disposable or sterilizable. In various examples, the linear members are affixed by a fractional-turn coupling, a threaded coupling, a quick-disconnect, a snap coupling, or other means of attaching. FIG. 21B illustrates detachable linear members in which each linear member is independently coupled to the device.

In the examples of FIGS. 21A and 21B, a cam mechanism can be provided to provide the opening and closing function of the linear members when used for stapling. The cam mechanism can include a cam surface, a slider, a roller, a pin in slot, or other mechanism.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
   a base structure having a distal end portion and a prismatic joint, the prismatic joint disposed along the distal end portion, wherein the prismatic joint includes a sliding member slidable along the distal end portion of the base structure;
   a handle member having a first pivot joint at a first end thereof, the first pivot joint coupled to the base structure, the handle member further having a second joint;
   the second joint coupled to a connecting member, the connecting member further rotatably coupled to a ternary link;
   the ternary link rotatably coupled to the sliding member, wherein the ternary link rotates with respect to the base structure upon actuation of the handle member.

2. The apparatus of claim 1, wherein the ternary link translates with respect to the base structure upon actuation of the handle member.

3. The apparatus of claim 1 wherein the sliding member is coupled to a flexible elongated member.

4. The apparatus of claim 3 wherein the flexible elongated member is housed within a first tube or a guide along at least a portion of its length.

5. The apparatus of claim 4 wherein the base structure has a grip portion and the flexible elongated member has a distal end portion configured to move distally relative to the base structure when the handle member is pivotally rotated toward the grip portion.

6. The apparatus of claim 5 wherein the flexible elongated member is sized and configured for insertion into a cavity of a human or animal.

7. The apparatus of claim 4 including a second tube that is substantially parallel to the first tube or guide.

8. The apparatus of claim 1, wherein the base structure further comprises a grip portion and the apparatus further comprises a stored energy element that stores energy as the handle member is pivotally rotated toward the grip portion.

9. The apparatus of claim 1 wherein the base structure has a pistol shape.

10. The apparatus of claim 1, wherein 30° of rotation of the handle member corresponds to approximately 4 inches of linear travel of the sliding member relative to the base structure.

11. The apparatus of claim 1 further comprising a fastener which is ejectable from the apparatus upon actuation of the handle member.

12. An apparatus comprising:
- a base structure having a prismatic joint to allow linear movement of a shaft;
- a handle having a first pivot joint at a first end coupled to the base structure and having a second pivot joint;
- a binary link having a first end coupled to the second pivot joint; and
- a ternary link coupled to a second end of the binary link, the ternary link coupled to the base structure by a pin in slot joint and coupled to the base structure by the prismatic joint.

13. The apparatus of claim 12 wherein the pin in slot joint includes a bearing coupled to a curved slot in the base structure.

14. The apparatus of claim 12 in which approximately 4 inches of linear movement corresponds to approximately 30 degrees of rotation of the handle.

15. The apparatus of claim 12 further comprising a fastener which is ejectable from the apparatus upon actuation of the handle.

* * * * *